United States Patent
Bean et al.

(10) Patent No.: US 6,849,577 B1
(45) Date of Patent: *Feb. 1, 2005

(54) AGROCHEMICAL FORMULATION

(75) Inventors: Michael John Bean, Bracknell (GB); Julia Lynne Ramsay, Bracknell (GB)

(73) Assignee: Syngenta Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/913,856

(22) PCT Filed: Jan. 28, 2000

(86) PCT No.: PCT/GB00/00249

§ 371 (c)(1),
(2), (4) Date: Nov. 6, 2001

(87) PCT Pub. No.: WO00/49873

PCT Pub. Date: Aug. 31, 2000

(30) Foreign Application Priority Data

Feb. 22, 1999 (GB) ............................................ 9904012

(51) Int. Cl.⁷ ................................................ A01N 25/30

(52) U.S. Cl. ....................... 504/127; 504/130; 504/363; 514/777; 514/785; 514/938; 514/975

(58) Field of Search .............................. 504/127, 130, 504/363; 514/777, 785, 938, 975

(56) References Cited

U.S. PATENT DOCUMENTS

| | | | | |
|---|---|---|---|---|
| 5,078,781 A | * | 1/1992 | Finch, Jr. | 71/94 |
| 6,010,979 A | * | 1/2000 | Osborn et al. | 504/206 |
| 6,117,820 A | * | 9/2000 | Cutler et al. | 504/206 |

FOREIGN PATENT DOCUMENTS

| | | | |
|---|---|---|---|
| EP | 0 388 239 | * | 9/1990 |
| EP | 0 487 262 | | 5/1992 |
| JP | 07-242510 | | 9/1995 |
| WO | 91/00010 | | 1/1991 |
| WO | 93/22917 | | 11/1993 |
| WO | 94/12259 | | 6/1994 |
| WO | 96/00010 | | 1/1996 |
| WO | 99/48359 | | 9/1999 |

* cited by examiner

Primary Examiner—S. Mark Clardy
(74) Attorney, Agent, or Firm—Thomas Hamilton

(57) ABSTRACT

A storage-stable aqueous agrochemical concentrate formulation comprises a) an agrochemical electrolyte such as glyphosate b) a water-insoluble agrochemical system such as diuron c) an alkylglycoside and d) a co-surfactant which interacts with the alkylglycoside to form a structured aqueous system. Examples of the co-surfactant include: i) a linear or branched chain aliphatic or aromatic alcohol or ii) an alcohol alkoxylate or ester alkoxylate or alkyl phenol alkoxylate iii) a glyceryl alkyl or alkenyl ester and iv) a sorbitan alkyl or alkenyl ester. The composition optionally contains an additional ionic surfactant.

15 Claims, No Drawings

AGROCHEMICAL FORMULATION

RELATED APPLICATIONS

This application is a § 371 of PCT/GB00/00249 filed 28 Jan. 2000, which claims priority to United Kingdom Application No. 9904012.3 filed 22 Feb. 1999.

The present invention relates to agrochemical formulations and in particular to aqueous formulations containing an agrochemical electrolyte and a suspended system.

It may often be desirable to combine different agrochemicals to provide a single formulation taking advantage of the additive properties of each separate agrochemical and optionally an adjuvant or combination of adjuvants that provide optimum biological performance. In commercial practice it is often desired to minimise transportation and storage costs by using a formulation in which the concentration of the active agrochemical(s) in the formulation is as high as is practicable and in which any desired adjuvants are "built-in" to the formulation as opposed to being separately tank-mixed. The higher the concentration of the active agrochemical(s) and its associated adjuvants however, the greater is the probability that the stability of the formulation may be disturbed and one or more component separates out. In general, the separation of a component from an agrochemical is highly undesirable, particularly when the formulation is sold in bulk containers. In these circumstances it is virtually impossible to re-homogenise the formulation and to achieve even distribution of the components on dilution and spraying. Furthermore, the formulation must be stable in respect of storage for prolonged periods in both hot and cold climates. These factors all present formidable problems to the formulator. The problems may be exacerbated still further if the formulation contains a water-soluble agrochemical electrolyte and a second agrochemical system which is water-insoluble. We have found that conventional anti-settling systems used to suspend water-insoluble agrochemicals, for example water-swellable clay suspending systems, may be rendered ineffective in the presence of a second agrochemical which is an electrolyte. Thus for example if a salt of glyphosate (a water-soluble agrochemical electrolyte) is added to an aqueous system in which a dispersion of the water-insoluble herbicide diuron is stabilised by a water-swellable clay, the dispersion may well be de-stabilised such that the diuron settles out of the formulation.

We have now found that it is possible to provide a stable agrochemical aqueous concentrate containing (i) a water-soluble agrochemical electrolyte (ii) a water-insoluble agrochemical system and (iii) a structuring system in which the compatibility problems of conventional suspending systems are overcome and that also offers formulation processing advantages.

Thus according to the present invention there is provided an aqueous agrochemical concentrate formulation comprising
a) an agrochemical electrolyte
b) a water-insoluble agrochemical system
c) an alkylglycoside
d) a co-surfactant which interacts with the alkylglycoside to form a structured aqueous system.

Whilst the scope of the present invention is not limited by any one particular theory as to the function of the components of the formulation, it is believed that the components, (and in particular the alkyl glycoside and the co-surfactant) interact to provide a structured aqueous system which acts to suspend the water-insoluble aqueous system. It is a particular advantage of the formulation of the present invention that the alkylglycoside not only provides one component of the suspending system but also acts as an adjuvant enhancing the biological activity of the agrochemical active ingredient. This is a significant advantage not only as a cost saving, but also because each additional component which has to be "built-in" to the formulation increases the stability problems. Thus having one single component, the alkylglycoside, which provides the radically different functions of a suspending agent and a biological activity enhancing adjuvant is a major and unexpected advance.

As examples of the co-surfactant which interacts with the alkylglycoside to form a structured aqueous system there may be mentioned compounds having a hydrophobic group in combination with a relatively small hydrophilic group for example:
i) a linear or branched chain aliphatic or aromatic alcohol or
ii) an alcohol alkoxylate or ester alkoxylate or alkyl phenol alkoxylate or
iii) a glyceryl alkyl or alkenyl ester or
iv) a sorbitan alkyl or alkenyl ester.

As used herein, the term alkyl, includes a linear or branched chain alkyl group and the term alkyl alcohol includes a linear or branched primary, secondary or tertiary alcohol. A linear or branched primary or secondary alkyl alcohol is generally preferred. As used herein, the term alkenyl, includes a linear or branched alkenyl group and the term alkenyl alcohol includes a linear or branched primary, secondary or tertiary alcohol. A linear or branched primary or secondary alkenyl alcohol is generally preferred.

The linear or branched chain alcohol (i) is preferably a primary or secondary, linear or branched alkyl or alkenyl alcohol containing from 5 to 20 carbon atoms or is a an alkyl-or alkenyl-substituted aromatic alcohol containing from 5 to 20 alkyl linear or branched carbon atoms, for example an alkylphenol containing from 5 to 20 alkyl carbon atoms. More preferably the alcohol is an alkyl alcohol containing from 5 to 12 carbon atoms or an alkenyl alcohol containing about 18 carbon atoms. As specific examples of suitable alcohols there may be mentioned pentanol, hexanol, octanol, octan-2-ol, decanol and their branched chain or mixture of branched chain equivalents and oleyl alcohol. As a specific example of a branched chain alcohol there may be mentioned 2-ethyl-1-hexanol. Although it is believed that the structuring of the aqueous phase is more than a mere viscosity effect, we have found that the viscosity of the formulation depends on the choice of alcohol. In general an excessively viscous formulation is less commercially desirable since it can be more difficult to handle a viscous formulation. We have found in particular that a branched alcohol such as 2-ethylhexanol gives effective dispersion through structuring of the aqueous phase whilst providing a relatively low-viscosity formulation even at low ambient temperatures. Octanol is a readily available and effective co-surfactant.

The alcohol, ester or alkyl phenol alkoxylate (co-surfactant (ii)) preferably has an alkoxide content of from 1 to 5, and more preferably from 1 to 3 $C_2$–$C_4$ alkoxy groups. The co-surfactant (ii) is preferably an alkoxylated $C_8$–$C_{22}$ alcohol, an alkoxylated $C_8$–$C_{22}$ alkyl phenol or an alkoxylated $C_8$–$C_{22}$ carboxylic acid each containing from 1–3 ethoxy groups. A suitable example is SYNPERONIC L2 which is based on lauryl alcohol with a mean ethylene oxide content of 2. A suitable example of the alkyl phenol alkoxylate is SYNPERONIC OP3 which is an ethoxylated octyl phenol with a mean degree of ethoxylation of 3.

As used herein (both generally and with specific reference to the alcohol or ester or alkyl phenol alkoxylate (ii)), the term "alkoxylated" includes both those compounds in which the alkoxy chain terminates in a hyroxyl group and those in which the alkoxy chain terminates in an alkyl group, such as a methyl group. Preferred alkoxyl groups are ethoxy or propoxy, and a mixture of alkoxy groups, for example a mixture of ethoxy and propoxy groups, may be present in the same alkoxylated molecule if desired.

The glyceryl alkyl or alkenyl ester (co-surfactant (iii)) is preferably a monoester of a $C_8$–$C_{22}$ carboxylic acid with glycerol. A suitable example is CITHROL GML which is glyceryl monolaurate.

The sorbitan alkyl or alkenyl ester preferably contains from 8 to 22 carbon atoms in the ester group, an especially suitable sorbitan ester is a sorbitan monolaurate such as that available under the trade name SPAN 20.

The water-soluble agrochemical electrolyte may be an active agrochemical or an agrochemical enhancer such as ammonium sulphate or any other ionic species added to an chemical formulation. The term "agrochemical" includes compounds which possess biological activity, for example herbicides, fungicides, nematocides, insecticides (optionally with an insecticide synergist) and plant growth regulators. Suitable agrochemical actives which are agrochemical electrolytes are glyphosate (N-phosphonomethylglycine), which is commonly used in the form of its water-soluble salts such as trimethylsulphonium, isopropylamine, sodium, or ammonium salts, fomesafen which is commonly used in the form of its water-soluble sodium salt, glufosinate which is commonly used in the form of its water-soluble ammonium salt, paraquat dichloride and bentazone which is commonly used in the form of its water-soluble sodium salt. The use of an agrochemical enhancer or other additive which is itself an electrolyte may still further enhance the ionic strength of the composition, thereby increasing the potential stability problems. Thus for example glyphosate salts are commonly formulated or tank-mixed with ammonium sulphate as an activity enhancer, whilst magnesium sulphate may be added to paraquat as a purgative as disclosed for example in EP 0467529.

The water-insoluble agrochemical system is preferably a water-insoluble agrochemical active ingredient or a water-insoluble system containing an agrochemical active ingredient. The term "water-insoluble" includes a component which is partially soluble in the aqueous concentrate such that at least a proportion thereof is present as an undissolved solid component. The term "water-insoluble system" includes any system which is required to be suspended in the aqueous formulation and which contains an agrochemical active ingredient regardless of whether that active ingredient is itself soluble or insoluble. Thus an example of a water-insoluble system is a microencapsulated formulation of a water-soluble or -insoluble agrochemical active ingredient. If the water-soluble agrochemical electrolyte is a herbicide such as glyphosate or paraquat, the agrochemical active present in the water-insoluble system will typically also be a herbicide, for example a water-insoluble herbicide. Typical water-insoluble herbicides include diuron, linuron, sulfometuron, chlorsulphuron, metsulfuron, chlorimuron, atrazine, simazine, quizalofop, butroxydim, nicosulfuron, primsulfuron, bensulfuron, ametryn, pendimethalin, isoproturon, chlortoluron, diflufenican, mesotrione, aclonifen, flurochloridone, oxyfluorfen, isoxaflutole, imazamox and thifensulfuron although the present invention does not depend critically on the nature of the water-insoluble agrochemical or herbicide and many others are published in the literature.

If a water-insoluble agrochemical (such as a herbicide) is used to prepare the aqueous concentrate of the present invention, it is conveniently incorporated in the form of a millbase (a finely divided suspension prepared by milling the solid agrochemical in water). The millbase will typically contain a minor proportion, for example from about 2% to about 10% weight based on the weight of solid agrochemical, of a dispersing agent to assist dispersion. The dispersing agent used in the millbase may be a cationic, anionic, amphoteric or non-ionic surfactant or polymer. However, as noted below, there are advantages in including a cationic surfactant in the formulation of the present invention and it is may be convenient therefore to use a cationic surfactant as dispersing agent in the millbase.

The alkylglycoside for use in the present invention may be obtained by the reaction of alkanols with glucose or other mono- or di- or polysaccharides. As used herein the term "alkylglycoside" includes an alkylmonoglycoside and an alkylpolyglycoisde. Preferred alkylglycosides for use in the present invention are alkylglucosides obtained by the reaction of glucose with a straight or branched chain alkanol or mixture of alkanols, for example a mixture of alkanols containing 7 to 18, preferably 7 to 16 carbon atoms for example 8 to 10 carbon atoms. The number of glycose groups per alkyl group in the molecule may vary and alkyl mono- or di- or polyglucose or saccharide derivatives are possible. Commercial alkylpolyglucosides usually contain a mixture of derivatives having an average number of glycose groups per alkyl group. Thus alkylglycosides have the general formula (I)

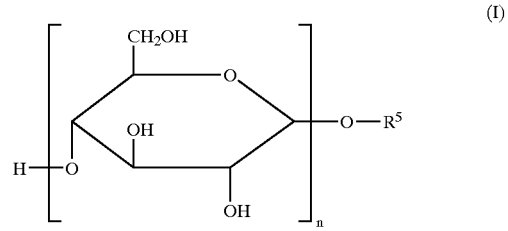

wherein n is the degree of polymerisation and is typically within the range from 1 to 3, for example from 1 to 2, and $R^5$ is a branched or straight chain alkyl group having from 4 to 18 carbon atoms or a mixture of alkyl groups having an average value within the given range. Typical of alkylglycosides is the product commercially available under the trade names AL2042 (Imperial Chemical Industries PLC and AGRIMUL PG2067 (Henkel Corp) wherein a is an average of 1.7 and $R^5$ is a mixture of octyl (45%) and decyl (55%), the product commercially available under the trade name AGRIMUL PG2069 (Henkel Corp) wherein n is an average of 1.6 and $R^5$ is a mixture of nonyl (20%), decyl (40%) and undecyl (40%) and the product commercially available under the trade name BEROL AG6202 (Akzo Nobel) which is 2-ethyl-1-hexylglycoside.

As indicated previously, the agrochemical formulations of the present invention are preferably stable at relatively high ambient temperatures. It has been found that enhanced high temperature stability may be obtained by the inclusion of a minor proportion of an ionic surfactant (component e) and it is believed that the presence of a minor proportion of an ionic surfactant in the formulation increases the amount of structuring that occurs, particularly at high temperatures. The addition of an ionic surfactant therefore offers another advantage, in that lower concentrations of the alkylglycoside and co-surfactant (d) can be used to produce stable formulations.

A wide range of suitable ionic surfactants (component e) will occur to those skilled in the art and those which have been found to enhance stability include cationic, anionic and amphoteric surfactants. Particularly suitable are cationic surfactants which include optionally ethoxylated amines, quaternary ammonium salts and amine oxides having at least one (for example 1, 2, 3 or 4) long chain (linear or branched) alkyl or alkenyl or alkyl aryl substituent(s) containing from 8 to 20 carbon atoms in the alkyl or alkenyl group and a preferred mean ethylene oxide content of from 0 to 20, even more preferably from 0 to 5. Particularly suitable anionic surfactants include alkyl sulphates, alkyl carboxylates, alkyl sulphosuccinates, alkyl phosphates and alkylbenzene sulphonates and their derivatives having at least one long chain alkyl or alkenyl substituent containing from 8 to 20 carbon atoms. In some instances the additional ionic surfactant may even provide an increase in the activity of the composition.

Especially preferred additional surfactants (component e) are cationic surfactants such as ethoxylated amines and optionally ethoxylated quaternary ammonium salts. Examples of suitable additional cationic surfactants include hexadecyl trimethyl ammonium chloride, coco trimethyl ammonium chloride and N-methyl cocoammonium chloride having a mean ethylene oxide content of 2.

As noted above, the advantages of the formulation of the present invention are fully realised at high concentrations of the agrochemical electrolyte such that, in the absence of the co-surfactant which interacts with the alkylglycoside to form a structured aqueous system (component d), one or more component is not satisfactorily suspended, thereby destroying the homogeneity of the concentration of the components within the formulation.

The agrochemical electrolyte glyphosate is especially suitable for formulation according to the present invention. Thus for example the present invention provides formulations of glyphosate wherein the concentration of glyphosate salt (expressed as glyphosate acid) is greater than 120 g/l and more particularly greater than 240 g/l, and most particularly greater than 300 g/l for example about 330 g/l or more.

The present invention provides excellent flexibility in the incorporation of the water-insoluble agrochemical system and it will generally be possible to include a wide range of proportions depending on the combined agrochemical effect it is desired to obtain. Thus the proportions may typically be from 150 parts by weight of agrochemical electrolyte to 1 part by weight of water-insoluble agrochemical system through to 1 part by weight of agrochemical electrolyte to 4 parts by weight of water-insoluble agrochemical system. The upper limit of the content of the water-insoluble agrochemical system is determined only by the proportion that can be effectively suspended and we have found for example that up to 500 g/l or more of a water-insoluble herbicide may generally be suspended in formulations of the present invention.

The co-surfactant (component d) present in the formulation is preferably from 0.1 parts by weight to 1 part by weight per 1 part by weight of alkylglycoside and most preferably from 0.2 parts by weight to 0.8 parts by weight of co-surfactant per 1 part by weight of alkyglycoside.

The proportion of additional ionic surfactant (component e) is preferably from 0 to 1 part by weight per 1 part by weight alkylglycoside and most preferably from 0.1 parts by weight to 0.3 parts by weight ionic surfactant per 1 part alkylglycoside. As noted above, a proportion of the additional ionic surfactant may initially be present as a dispersing agent in a millbase of a water-insoluble agrochemical.

In general, it is preferred that the total proportion of alkoxylated surfactant present (either as component (e) or as a dispersing agent for the water-insoluble agrochemical) will be below the concentration which would undergo phase separation in the absence of the structuring provided by the co-surfactant (d).

The proportion by weight of the total adjuvant or structuring system (i.e. components (c) (d) and (e) if used) to the agrochemical electrolyte is preferably from 4:1 to 1:10 and especially from 1:1 to 1:4.

Other additives, humectants or additional adjuvants may also be present in compositions of the present invention. Examples include anti-freeze agents such as ethylene glycol, urea and propylene glycol; dyes; polymers; dispersants; theological agents; and anti-foam agents such as silicone based agents. If any such additional component, whether a liquid or an insoluble solid, itself has a tendency to phase separate or settle from the composition, the structured phase provided by the present invention will additionally serve to keep such additional component homogeneously distributed throughout the formulation.

Compositions of the present invention provide adjuvant enhancement for the active agrochemicals concerned or increase the effectiveness of the adjuvant if the agrochemical electrolyte is an agrochemical enhancer such as ammonium sulphate. Thus formulations of the invention wherein the agrochemical electrolyte is a herbicide, and in particular when the herbicide is glyphosate, are active against a broad range of weed species including monocotyledonous and dicotyledonous species.

Thus according to a further aspect of the present invention wherein the agrochemical electrolyte is a herbicide, there is provided a process of severely damaging or killing unwanted plants which comprises applying to the plants a herbicidally effective amount of a composition of the present invention.

The rate of application of the composition of the invention will depend on a number of factors including, for example, the active ingredients chosen for use, the identity of the, plants whose growth is to be inhibited and the formulations selected for use and whether the compound is to be applied for foliage or root uptake. As a general guide, however, an application rate of from 0.001 to 20 kilograms per hectare is suitable while from 0.025 to 10 kilograms per hectare may be preferred.

We have found that the development of a structured aqueous phase and a homogeneous dispersion which gives a uniform distribution in respect of all the components within the formulation, is not critically dependent on the method of preparation of the formulation. It is preferred however that structuring of the system does not take place (i.e. the alkylglycoside and co-surfactant (d) are not brought together) until all the other components, and in particular the water-insoluble system, are effectively dispersed. Whilst it would be possible to add the alkylglycoside to all the other components, including the co-surfactant (d), it is normally simpler to admix all the components apart from the co-surfactant (d) which is only added once an effective dispersion has been obtained. It will be appreciated that before structuring takes place the formulation is relatively free-flowing so that for example the millbase of an insoluble herbicide is readily dispersed. Once structuring takes place, the dispersion is held in stable suspension.

Thus according to a further aspect of the present invention there is provided a method for forming an aqueous agrochemical concentrate formulation which comprises bringing into admixture an aqueous dispersion of a) an agrochemical electrolyte
b) a water-insoluble agrochemical system and
c) an alkylglycoside and optionally e) an ionic surfactant and thereafter adding d) a co-surfactant which interacts with the alkylglycoside to form a structured aqueous system.

It is a particular advantage of the method of the present invention that the structuring of the system can be accomplished using a low shear mixer to incorporate the co-surfactant Thus effective dispersion can typically be achieved using a simple paddle stirrer. In contrast, prior art systems that use a water-swellable clay and/or polysaccharide gels, require high-shear mixing to disperse either the millbase into a pre-structured system or the clays/polysaccharides (unswollen or pre-swelled) into the millbase Factors such as this add considerably to the cost of preparing a formulation on a commercial scale. Furthermore, we have found that preferred ionic surfactants such as ARQUAD 16-29 which would otherwise improve the performance of the electrolyte formulation may themselves be incompatible with water-swellable clays resulting in an unstable formulation.

The order of addition of components (a), (b) and (c) (and (e) if used) is not important provided that structuring of the system takes place once effective dispersion has been achieved.

In general, we have not encountered significant problems in diluting the formulation of the present invention ready for agrochemical use, although excessively viscous or excessively structured compositions may require care to ensure that the concentrate has been effectively dispersed in the water of dilution before use.

The invention is illustrated by the following Examples in which all parts and percentages are by weight unless otherwise stated. The description of commercially available surfactants is given below.

AGRIMUL PG 2067 is a 70% w/w solution of alkylpolyglycoside of formula (I) above wherein n is an average of 1.7 and $R^5$ is a mixture of octyl (45%) and decyl (55%). AGRIMUL is a trademark of Henkel.

ARQUAD 16-29 is a 29% by weight solution of hexadecyl trimethyl ammonium chloride in water. ARQUAD is a trademark of Akzo Nobel.

TETRONIC 1307 is an ethoxylated/propoxylated diamine with 70% ethylene oxide and a molecular weight of 18,000. Tetronic is a trademark of BASF.

BENTOPHARM B20 is a bentonite clay. Bentopharm is a trademark of Bromhead and Dennison KELZAN M is a xanthum gum. Kelzan is a trademark of Monsanto.

SYNPERONIC L2 is an ethoxylated lauryl alcohol having a mean degree of ethoxylation of 2. SYNPERONIC is a trademark of Imperial Chemical Industries.

EXAMPLE 1

A composition according to the present invention was prepared as follows:—

To an aqueous solution of paraquat dichloride was added AGRIMUL PG 2067 and makeup water with mixing. Once a homogenous solution was obtained, diuron millbase containing ARQUAD 16-29 as dispersant was added with mixing. A homogeneous dispersion was readily obtained and thereafter octanol was added with mixing to provide a structured system.

The proportions of the components in the final composition were as follows:—

| Example 1 | |
|---|---|
| Paraquat dichloride (expressed as paraquat ion) | 150 g/l |
| Diuron | 150 g/l |
| ARQUAD 16-29 (expressed as the active surfactant) | 15 g/l |
| AGRIMUL PG2067 (expressed as the active surfactant) | 105 g/l |
| Octanol | 30 g/l |
| Water | to 1 liter |

The resultant structured composition was tested for physical stability at −5, 25 & 40° C. respectively and remained stable under all these conditions when observations were discontinued after 15 weeks.

EXAMPLE 2

The procedure of Example 1 was followed to give the following composition:

| Example 2 | |
|---|---|
| Glyphosate trimesium (expressed as glyphosate acid) | 200 g/l |
| Diuron | 200 g/l |
| ARQUAD 16-29 added in the diuron millbase (expressed as the active surfactant) | 20 g/l |
| AGRIMUL PG2067 (expressed as the active surfactant) | 98 g/l |
| Octanol | 28 g/l |
| Water | to 1 liter |

The resultant structured composition was tested for physical stability at −5, 25 & 40° C. respectively and remained stable under all these conditions when observations were discontinued after 14 weeks.

Comparison 1

This comparison illustrates that conventional diuron dispersions may be structured using a KELZAN/BENTOPHARM suspending system but can lose stability in the presence of an agrochemical electrolyte. The diuron millbase contained TETRONIC 1307 as a dispersant which is compatible with the KELZAN/BENTOPHARM suspending system. It was found that a high-shear stirrer was necessary to provide an effective dispersion of the KELZAN/BENTOPHARM suspending system.

| Comparison 1A | |
|---|---|
| Diuron | 150 g/l |
| TETRONIC 1307 added in the diuron millbase (expressed as the active surfactant) | 15 g/l |
| BENTOPHARM B20 (10% in water-expressed as Bentonite clay) | 15 g/l |
| KELZAN M (2% in water-expressed as xanthum gum) | 2 g/l |
| Water | to 1 liter |

The resultant composition was tested for physical stability at −5, 25 & 40° C. respectively. The composition froze at −5° C. but remained stable at 25 and 40° C. when observations were discontinued after 5 weeks.

| Comparison 1B | |
|---|---|
| Paraquat dichloride (expressed as paraquat ion) | 150 g/l |
| Diuron | 150 g/l |
| TETRONIC 1307 added in the diuron millbase (expressed as the active surfactant) | 15 g/l |
| BENTOPHARM B20 (10% in water-expressed as bentonite clay)) | 15 g/l |
| KELZAN M (2% in water-expressed as xanthum gum) | 2 g/l |
| Water | to 1 liter |

The resultant composition was tested for physical stability at −5, 25 & 40° C. respectively. Compositions were found to be unstable at all temperatures after 4 days.

Comparison 2

This comparison illustrates that a composition equivalent to that of Example 2 but using a KELZAN/BENTOPHARM suspending system in place of that of the present invention is unstable after only 1 week. Furthermore, even in the absence of the electrolyte glyphosate trimesium, the composition is unstable, it is believed as a result of an adverse interaction of the preferred ARQUAD 16-29 dispersant and the KELZAN/BENTOPHARM suspending system.

| Comparison 2A | | Comparison 2B | |
|---|---|---|---|
| Glyphosate trimesium (expressed as glyphosate acid) | 200 g/l | | |
| Diuron | 200 g/l | Diuron | 200 g/l |
| ARQUAD 16–29 (expressed as the active surfactant) | 20 g/l | ARQUAD 16–29 (expressed as the active surfactant) | 20 g/l |
| BENTOPHARM B20 (10% in water-expressed as bentonite clay) | 15 g/l | BENTOPHARM B20 (10% in water-expressed as bentonite clay) | 15 g/l |
| KELZAN M (2% in water-expressed as xanthum gum) | 2 g/l | KELZAN M (2% in water-expressed as xanthum gum) | 2 g/l |
| Water | to 1 liter | Water | to 1 liter |

Comparisons 2A and 2B were found to be unstable after between 4 days and 1 week at 25 and 40° C.

EXAMPLE 3

This Example illustrates the beneficial effect of adding a quaternary ammonium salt (hexadecyl trimethyl ammonium chloride) as an additional ionic surfactant (component (e)). Formulations were prepared using the general method of Example 1 according to the following composition:—

| Example 3 | |
|---|---|
| Glyphosate trimesium (expressed as glyphosate acid) | 350 g/l |
| Diuron | 100 g/l |
| ARQUAD 16–29 added in the diuron millbase (expressed as the active surfactant) | 10 g/l |
| Additional ARQUAD 16–29 (expressed as the active surfactant) | X g/l |

-continued

| Example 3 | |
|---|---|
| AGRIMUL PG2067 (expressed as the active surfactant) | 35 g/l |
| Octanol | 10 g/l |
| Water | to 1 liter |

Conditions were deliberately chosen to be testing with a high concentration of glyphosate trimesium and a concentration of alkylglycoside well below that considered as optimum. The quantity of ARQUAD 16-29 added in the diuron millbase was equivalent to 10 g/l. Under these exceptional conditions, the composition failed the stability test when no additional ARQUAD 16-29 was added (C in the above Table is 0). However as additional quantities of ARQUAD 16-29 were added (20, 30 and 40 g/l respectively) the stability of the composition progressively improved. This improvement is illustrated in the following Table which shows the stability of the composition as a function of the added ARQUAD 16-29 (X g/l in the above Table). Stability was measured after 3.5 weeks at −5, 25 and 40° C. respectively.

| | Temperature | | |
|---|---|---|---|
| X (g/l) | −5° C. | 25° C. | 40° C. |
| 0 | Top separation only | Catastrophic separation | Catastrophic separation |
| 20 | Partial separation | Trace of top separation | Trace of top separation |
| 30 | Top separation and streaking | Top separation only | Homogeneous |
| 40 | Homogeneous | Homogeneous | Homogeneous |

EXAMPLE 4

This Example illustrates the use of SYNPERONIC L2 as co-surfactant (component d). The following composition was prepared using the general method of Example 1:—

| Example 4 | |
|---|---|
| Glyphosate trimesium (expressed as glyphosate acid) | 200 g/l |
| Diuron | 200 g/l |
| ARQUAD 16–29 added in the diuron millbase (expressed as the active surfactant) | 20 g/l |
| AGRIMUL PG2067 (expressed as the active surfactant) | 63 g/l |
| SYNPERONIC L2 | 45 g/l |
| Water | to 1 liter |

The resultant structured composition was tested for physical stability at −5, 25 & 40° C. respectively and remained stable under all these conditions when observations were discontinued after 4 weeks.

What is claimed is:

1. An aqueous agrochemical concentrate formulation comprising
    a) an agrochemical electrolyte,
    b) a water-insoluble agrochemical system,
    c) an alkyglycoside, and
    d) a co-surfactant which interacts with the alkyglycoside to form a structured aqueous system
       wherein the co-surfactant (d) is i) a linear or branched chain aliphatic or aromatic alcohol or ii) an alcohol or ester or alkyl phenol alkoxylate which is an alkoxylated $C_8$–$C_{22}$ alcohol, an alkoxylated $C_8$–$C_{22}$ alkyl phenol or an alkoxylated $C_8$–$C_{22}$ carboxylic acid each containing from 1–3 alkoxy groups or iii) a glyceryl alkyl or alkenyl ester.

2. The formulation according to claim 1 wherein:

the linear or branched chain alcohol (i) is a primary or secondary, linear or branched alkyl or alkenyl alcohol containing from 5 to 20 carbon atoms or is an alkyl- or alkenyl-substituted aromatic alcohol containing from 5 to 20 linear or branched alkyl carbon atoms; or wherein the alcohol or ester or alkyl phenol alkoxylate (ii) is an alkoxylated $C_8$–$C_{22}$ primary or secondary, linear or branched chain alcohol, an alkoxylated $C_8$–$C_{22}$ alkyl phenol or an alkoxylated $C_8$–$C_{22}$ carboxylic acid each containing from 1–3 $C_2$–$C_4$ alkoxy groups; or wherein the glyceryl alkyl or alkenyl ester (iii) is a monoester of a $C_8$–$C_{22}$ carboxylic acid with gylerol.

3. The formulation according to claim 2, wherein the co-surfactant comprises at least one member selected from the group consisting of pentanol, hexanol, octanol, octan-2-ol, decanol and their branched chain or mixture of branched chain equivalents, oleyl alcohol, 2-ethyl-1-hexanol, an ethoxylated lauryl alcohol having a mean ethylene oxide content of 2, an ethoxylated octyl phenol having a mean degree of ethoxylation of 3, and glyceryl monolaurate.

4. The formulation according to claim 1, wherein the agrochemical electrolyte comprises at least one member selected from the group consisting of salts of glyphosate, fomesafen, glufosinate, paraquat and bentazone or is ammonium sulphate.

5. The formulation according to claim 1, wherein the water-insoluble agrochemical system comprises an agrochemical active ingredient.

6. The formulation according to claim 5, wherein the water-insoluble system is a water-insoluble herbicide.

7. The formulation according to claim 6, wherein the water-insoluble herbicide comprises at least one member selected from the group consisting of diuron, linuron, sulfometuron, chlorsulphuron, metsulfuron, chlorimuron, atrazine and simazine.

8. The formulation according to claim 1, further comprising a cationic, anionic or amphoteric surfactant.

9. The formulation according to claim 8, wherein the cationic surfactant comprises at least one linear or branched long chain alkyl or alkenyl or alkyl aryl substituent containing from 8 to 20 alkyl or alkenyl carbon atoms and a mean ethylene oxide content of from 0 to 20 which is an optionally ethoxylated amine, quaternary ammonium salt or amine oxide; or wherein the anionic surfactant comprises at least one long chain alkyl or alkenyl substituent containing from 8 to 20 carbon atoms which is an alkyl sulphate, alkyl carboxylate, alkyl sulphosuccinate, alkyl phosphate or alkylbenzene sulphonate and derivatives thereof.

10. The formulation according to claim 1, wherein the water-insoluble agrochemical system is present in a proportion of from 150 parts by weight of agrochemical electrolyte to 1 part by weight of water-insoluble agrochemical system to 1 part by weight of agrochemical electrolyte to 4 parts by weight of water-insoluble agrochemical system.

11. The formulation according to claim 1, wherein the proportion of the co-surfactant is from 0.1 parts by weight to 1 part by weight per 1 part by weight of alkylglycoside.

12. The formulation according to claim 8, wherein the proportion of cationic, anionic or amphoteric surfactant is from 0 parts by weight to 1 parts by weight cationic, anionic or amphoteric surfactant per 1 part alkyglycoside.

13. The formulation according to claim 8, wherein the proportion by weight of the total of the alkyglycoside, the cosurfactant and cationic, anionic or amphoteric surfactant to the agrochemical electrolyte is from 4:1 to 1:10.

14. A process for severely damaging or killing unwanted plants comprising applying to the plants a herbicidally effective amount of the formulation according to claim 1, wherein the agrochemical electrolyte is a herbicide.

15. A process for the preparation of the formulation according to claim 1 which comprises bringing into admixture an aqueous dispersion of a) an agrochemical electrolyte, b) a water-insoluble agrochemical system, c) an alkylglycoside, and e) optionally an ionic surfactant, and thereafter adding d) a co-surfactant which interacts with the alkylglycoside to form a structured aqueous system wherein the co-surfactant (d) is i) a linear or branched chain aliphatic or aromatic alcohol or ii) an alcohol or ester or alkyl phenol alkoxylate which is an alkoxylated $C_8$–$C_{22}$ alcohol, an alkoxylated $C_8$–$C_{22}$ alkyl phenol or an alkoxylated $C_8$–$C_{22}$ carboxylic acid each containing from 1–3 alkoxy groups alkenyl ester.

* * * * *